United States Patent
Cheong et al.

(10) Patent No.: US 10,588,928 B2
(45) Date of Patent: Mar. 17, 2020

(54) ANTI-OBESITY COMPOSITION COMPRISING PINE NEEDLE JUICE POWDER AS EFFECTIVE COMPONENT

(71) Applicant: INDUSTRY-ACADEMIC COOPERATION FOUNDATION, CHOSUN UNIVERSITY, Gwangju (KR)

(72) Inventors: Hyeonsook Cheong, Gwangju (KR); Woong Kim, Gwangju (KR); Jaeyoung Park, Gwangju (KR); Beomgi Lee, Gwangyang-si (KR); Cheolwoo Park, Gwangju (KR)

( * ) Notice: Subject to any disclaimer, the term of this patent is extended or adjusted under 35 U.S.C. 154(b) by 247 days.

(21) Appl. No.: 15/713,706

(22) Filed: Sep. 25, 2017

(65) Prior Publication Data
US 2018/0085412 A1 Mar. 29, 2018

(30) Foreign Application Priority Data
Sep. 26, 2016 (KR) .................. 10-2016-0123180

(51) Int. Cl.
*A61K 36/15* (2006.01)
*A61K 9/19* (2006.01)

(52) U.S. Cl.
CPC ............. *A61K 36/15* (2013.01); *A61K 9/19* (2013.01); *A61K 2236/15* (2013.01); *A61K 2236/51* (2013.01)

(58) Field of Classification Search
None
See application file for complete search history.

(56) References Cited

U.S. PATENT DOCUMENTS 7,135,199 B2 * 11/2006 Kim .................. A61K 36/8962
424/725

FOREIGN PATENT DOCUMENTS

| CN | 104223251 A | * 12/2014 |
|---|---|---|
| KR | 1020020016197 A | 3/2002 |
| KR | 1020040089258 A | 10/2004 |
| KR | 10-0813187 B1 | * 3/2008 |

* cited by examiner

*Primary Examiner* — Susan Hoffman
(74) *Attorney, Agent, or Firm* — Chanmin Park

(57) ABSTRACT

An anti-obesity composition comprises pine needle juice powder as an effective component. Because it is found that, not only a significantly higher extraction yield is obtained and a higher inhibitory activity on differentiation of an adipocyte is obtained when an extract is produced by using pine needle juice powder obtained by juicing process instead of using dry pine needle which has not been treated with any juicing process, but also both the body weight and weight of white adipose tissues are lowered and content of total lipid, total cholesterol, and triglyceride in blood is significantly lowered according to oral administration of the pine needle juice powder of the present invention to a model mouse under high fat diet, the pine needle juice powder of the present invention can be more advantageously used for a pharmaceutical composition or a functional health food for prophylaxis or treatment of obesity.

9 Claims, 7 Drawing Sheets

ANTI-OBESITY COMPOSITION COMPRISING PINE NEEDLE JUICE POWDER AS EFFECTIVE COMPONENT

STATEMENT REGARDING GOVERNMENT SPONSORED RESEARCH

This work was supported by Korea Institute of Planning and Evaluation for Technology in Food, Agriculture, Forestry(IPET) through High Value-added Food Technology Development Program, funded by Ministry of Agriculture, Food and Rural Affairs (MAFRA) (116010-03).

TECHNICAL FIELD

The present invention relates to an anti-obesity composition which comprises pine needle juice powder as an effective component.

BACKGROUND ART

Due to the high standard of living in recent years, there is a new trend in food consumption, i.e., intake of fats and carbohydrates increases while intake of fibers decreases. In particular, as eating outside the home becomes quite popular, a phenomenon of people preferring high-protein food is clearly exhibited. Meanwhile, due to a modern day lifestyle with almost no physical activity, obese population rapidly increases in current days. Namely, as the intake of high calorie food increases while intake of fibers decreases, obesity, in particular, abdominal obesity, is noted as a significant social problem. Obesity indicates a state in which adipose tissues have excessively increased, and the increase in body weight related with obesity is mostly caused by increased fats.

Obesity is a metabolic disease which occurs due to imbalance between intake and consumption of calorie, in which adipose tissues are increased to an abnormal level due to excessive calorie. If obesity occurs and a person continues to remain in an obese state, various diseases are caused. For example, it is known that hypertension, an increase in blood cholesterol, diabetes, kidney disease, brain stroke, arteriosclerosis, fatty liver, arthritis, cancer, sleep apnea, or the like are caused by obesity.

Obesity is caused by accumulation of triglycerides (TG) in an adipocyte according to differentiation of preadipocyte and adipogenesis, and regulating the mechanism of adipogenesis is known as a therapeutic method which is effective for suppression of obesity. However, because existing therapeutic agents for obesity have only a weak effect or various side effects, they are taken by only a small number of patients with obesity. As an anorectic agent which works on a central nervous system, there are phentermine which is a noradrenaline-based pharmaceutical, fluoxetine which is a serotonin-based pharmaceutical, sibutramine which is a mixture of noradrenaline-based pharmaceutical and a serotonin-based pharmaceutical, and the like, and also orlistat which is a pharmaceutical for suppressing absorption of nutrients, and rimonabant, taranabant, or the like which are an endogeneous cannabinoid receptor antagonist. However, those therapeutic agents for obesity cause a side effect including mental disorder such as depression, anxiety, or insomnia, and nausea, dizziness, diarrhea, constipation, and hypertension. In particular, rimonabant and sibutramine are currently no longer commercially available due to their side effects, and at present moment, only orlistat, belviq, and qsymia are approved by FDA and commercially available.

As such, it is required to develop, from natural products that are expected to have relatively minimum possibility of causing problems related with safety, a pharmaceutical for treating obesity which has a high anti-obesity effect with minor side effect. Namely, it is required to found a material derived from natural products which can inhibit the differentiation process of an adipocyte while having a minor side effect.

Meanwhile, in Korean Patent Application Publication No. 2004-0089258, a composition for treating obesity and constipation comprising an extract of pine needle, green tea, and red tea is disclosed. In Korean Patent No. 0470204, a composition for suppressing obesity comprising an extract of galenic materials and a health supplementary food comprising it as an effective component are described. However, the technology relating to an anti-obesity composition comprising pine needle juice powder as an effective component as described in the present invention has not been disclosed yet.

DETAILED DESCRIPTION OF THE INVENTION

Technical Problems to be Solved

The present invention is devised in view of the circumstances described above, and as it is confirmed in the present invention that significant higher extraction yield is obtained when an extract is produced by using pine needle juice powder that is obtained by a juicing process instead of using dry pine needle which has not been treated with any juicing process, and, when 3T3-L1 preadipocyte is treated with an extract of the pine needle juice powder, a more significant effect of inhibiting adipocyte differentiation is obtained compared to an extract of dry pine needle. It is also confirmed that, as a result of oral administration of pine needle juice powder to a model mouse under high fat diet, both the body weight and weight of white adipose tissues are lowered, and also content of total lipid, total cholesterol, and triglyceride in blood is significantly lowered, and thus the present invention is completed accordingly.

Technical Means for Solving the Problems

To solve the problems described above, the present invention provides a functional health food composition for preventing or improving obesity comprising pine needle juice powder as an effective component.

The present invention also provides a pharmaceutical composition for preventing or treating obesity comprising pine needle juice powder as an effective component.

Advantageous Effect of the Invention

The present invention relates to an anti-obesity composition which comprises pine needle juice powder as an effective component. Because it is found that, not only a significantly higher extraction yield is obtained and a higher inhibitory activity on differentiation of an adipocyte is obtained when an extract is produced by using pine needle juice powder obtained by juicing process instead of using dry pine needle which has not been treated with any juicing process but also both the body weight and weight of white adipose tissues are lowered and content of total lipid, total cholesterol, and triglyceride in blood is significantly lowered according to oral administration of the pine needle juice powder of the present invention to a model mouse under high fat diet, the pine needle juice powder of the present invention can be more advantageously used for a pharmaceutical composition or a functional health food for prophylaxis or treatment of obesity.

BEST MODE(S) FOR CARRYING OUT THE INVENTION

Figure 1:
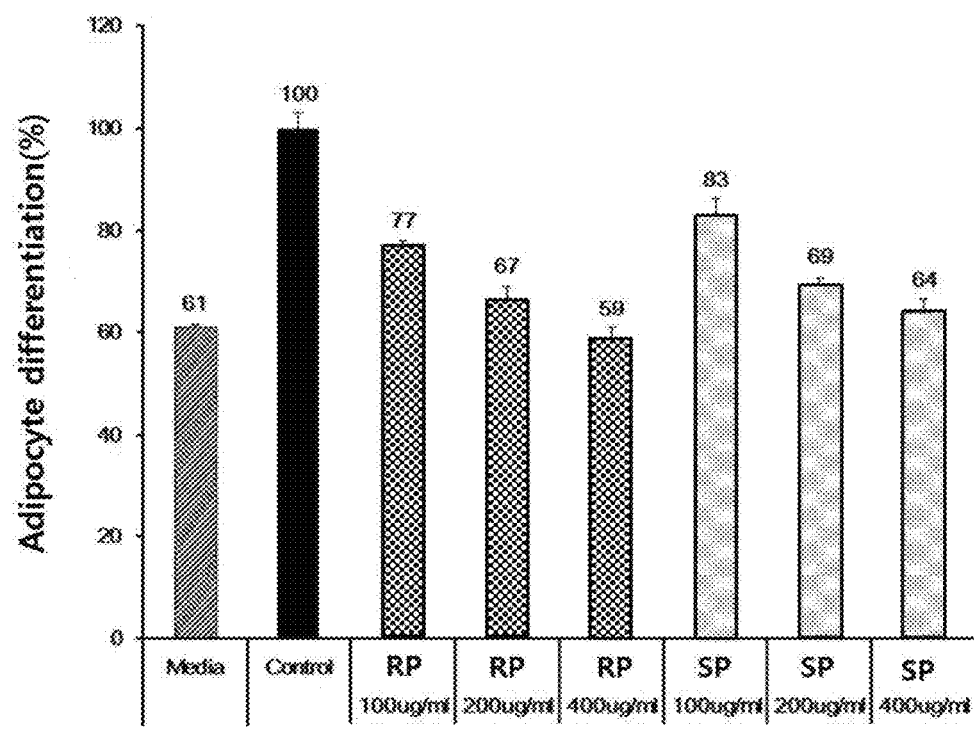
FIG. 1 is a drawing illustrating the inhibitory activity on differentiation of an adipocyte when 3T3-L1 preadipocyte is treated with an extract of pine needle juice powder of red pine tree(RP)(Pinus densiflora) or sea pine tree(SP) (Pinus thunbergii) according to one embodiment of the present invention. Media represents a control group which has been treated only with BCS (bovine calf serum) medium and Control represents a control group which has been treated with MDI (insulin, dexamethasone, and IBMX) as a material for inducing lipid differentiation.

The present invention provides a method of preventing or treating obesity, the method comprising administering a composition comprising a pine needle juice powder to a subject having the obesity.

To achieve the purpose of the present invention, the present invention provides a functional health food composition for preventing or improving obesity comprising pine needle juice powder as an effective component.

With regard to the functional health food composition for preventing or improving obesity of the present invention, the pine needle juice powder may be the powder which has been produced by the following steps:
1) preparing pine needle juice by juicing pine needles;
2) freeze-drying the pine needle juice of the above step 1); and
3) pulverizing a freeze-dry product of the pine needle juice obtained by freeze-drying in the above step 2) to give pine needle juice powder, but the pine needle juice powder is not limited thereto.

Furthermore, a step of extracting the pine needle juice powder may be further included after the above step 3), but it is not limited thereto.

Furthermore, the extraction of pine needle juice powder can be an extraction which is carried out by ultrasonication for 12 to 20 hours at a temperature of 50 to 70° C. by using water, lower alcohol with 1 to 4 carbon atoms, or a mixture solvent thereof, and it is preferably hot water extraction or 95% (v/v) ethanol extraction that is carried out by ultrasonication for 16 hours at a temperature of 60° C., but not limited thereto.

Furthermore, the pine needle may be a pine needle of red pine (Pinus densiflora), but not limited thereto.

For the purpose of preventing or improving obesity, the pine needle juice powder of the present invention may be added to a food or a beverage. The functional health food composition of the present invention comprises the pine needle juice powder as an effective component, and other components which may be included are not particularly limited. Examples of the component which may be comprised as an additional component include various flavoring agents and natural carbohydrates, like a common food and beverage. Examples of the natural carbohydrates include common sugars including monosaccharides such as glucose or fructose; disaccharides such as maltose or sucrose; and polysaccharides such as dextrin or cyclodextrin, and sugar alcohols such as xylitol, sorbitol, or erythritol.

Other than those described above, the pine needle juice powder of the present invention may contain various kinds of a nutritional agent, vitamin, an electrolyte, a flavoring agent including synthetic flavoring agent and artificial flavoring agent, a coloring agent, an enhancing agent (cheese, chocolate, and the like), pectinic acid and a salt thereof, alginic acid and a salt thereof, an organic acid, a protective colloidal thickening agent, a pH adjusting agent, a stabilizer, a preservative, glycerin, alcohol, and a carbonating agent used for carbonate drink. In addition, the pine needle juice powder of the present invention may contain fruit flesh for producing natural fruit juice, fruit juice drink, or vegetable drink. Those components may be used either separately or in combination thereof. Ratio of those additives is not so important. However, they are generally selected within a range of 0 to 20 parts by mass approximately relative to 100 parts by mass of the pine needle juice powder of the present invention.

With regard to a health food for preventing or improving obesity according to one embodiment of the present invention, the food may be selected from the group consisting of a dairy product, fermented milk, a drink, a meat product, sausage, bread, chocolate, candies, snacks, cookies, pizza, ramen, gums, ice cream, soup, beverages, alcohol beverages, and vitamin complex, but not limited thereto.

The present invention also provides a pharmaceutical composition for preventing or treating obesity comprising pine needle juice powder as an effective component.

With regard to the pharmaceutical composition for preventing or treating obesity of the present invention, the pine needle juice powder may be powder which inhibits differentiation of an adipocyte, but not limited thereto.

The composition comprising the pine needle juice powder of the present invention may further comprise a suitable carrier, excipient, or diluent commonly used for preparation of a pharmaceutical composition.

As for the pharmacological administration form of the pine needle juice powder of the present invention, it may be used not only in single form or in combination with other pharmaceutically active compounds but also in a suitable group with them.

The composition comprising the pine needle juice powder of the present invention may be used after formulation into an orally administered formulation including a powder preparation, a granule, a tablet, a capsule, a suspension, an emulsion, a syrup, and an aerosol, or formulation into a preparation for external application, a suppository, or a sterile solution for injection.

Examples of the carrier, vehicle, and diluent which may be included in the composition comprising the pine needle juice powder include various compounds including lactose, dextrose, sucrose, sorbitol, mannitol, xylitol, erythritol, maltitol, starch, acasia gum, alginate, gelatin, calcium phosphate, calcium silicate, cellulose, methyl cellulose, microcrystalline cellulose, polyvinyl pyrrolidone, water, methyl hydroxyl benzoate, propyl hydroxyl benzoate, talc, magnesium stearate, and mineral oil, and a mixture thereof.

At the time of formulation, a commonly used diluent or an excipient such as a filler, a volume expanding agent, a binding agent, a wetting agent, a disintegrating agent, or a surfactant is used for production. A solid preparation for oral administration includes a tablet, a pill, powder, a granule, and a capsule, and those solid formulations are prepared by mixing the pine needle juice powder with at least one vehicle such as starch, calcium carbonate, oligosaccharides, sucrose, lactose, or gelatin. Furthermore, a lubricating agent such as magnesium stearate or talc can be used in addition to a simple vehicle. Examples of a liquid formulation for oral administration include a suspension, a solution, an emulsion, and a syrup, and in addition to water, liquid paraffin or the like that are commonly used, various vehicles such as a wetting agent, a sweetening agent, an aroma, a preservative, or the like may be included. Examples of the formulation for parenteral administration include a sterilized aqueous solution, a non-aqueous solution, a suspension, an emulsion, a freeze dry product, and a suppository. For a non-aqueous solution and a suspension, propylene glycol, polyethylene glycol, vegetable oils like olive oil, and injectable esters like ethylolate can be used. As a base of a suppository, witepsol, Macrogol, Tween 61, cacao fat, laurin fat, glycerogelatin or the like can be used.

A preferred dosage of the pine needle juice powder of the present invention may vary depending on a state and body weight of a patient, degree of symptoms, dosage form, administration route, and administration period. However, it may be suitably selected by a person skilled in the art.

The pine needle juice powder of the present invention may be administered via various routes to a mammal including rat, mouse, livestock, and human. It is expected to employ any kind of administration mode, and examples of the administration mode include oral, rectal, intravenous, intramuscular, subcutaneous, uterine epidural, and intracerebroventricular injection. However, it is preferable to have oral administration.

Herein below, the present invention is explained in greater detail in view of the Examples. However, it would be evident for a person having common knowledge in the pertinent art that the following Examples are given only for specific exemplification of the present invention and by no means the scope of the present invention is limited to those examples.

EXAMPLES

[Materials and Methods]
1. Preparation of pine needle juice powder and extract thereof For pine needles, healthy red pine (Pinus densiflora) grown in Goksung, Jeonlanam-Do, South Korea (at least 350 m above sea level) was selected, tree branches in good nutritional state were collected, and only fresh green needles were collected and used. The selected pine needles were cleaned several times. After completely removing the moisture on surface of needles by using a dehydrator, juice was extracted by using a large juicing machine (200 kg, prepared by the inventors using compartments of Inwha Precision, Samkwang Mooryok Gongsa, Myungshin Sangsa, and Green Juicing machine). No other additives than pine needle were added therefor, and the pine needle juice extract was subjected to pre-freeze drying at −50° C., and then kept in the freeze dryer. By operating a vacuum pump at −70 to −85° C., moisture was completely removed from the juice extract, which was then kept until it is brought back to the room temperature. The obtained dry product was pulverized using a mixer to prepare fine powder of pine needle juice extract.

The pine needle juice powder was subjected to hot water extraction and 95% (v/v) ethanol extraction. Specifically, the extraction was made for 16 hours at a temperature of 60° C. using a sonic wave generator (Powersonic410, Hwason Tech). For a control group, dried pine needles were subjected to hot water extraction and 95% (v/v) ethanol extraction in the same manner as the present invention except that no juicing process is carried out therefor. Specifically, the extraction was made for 16 hours at a temperature of 60° C. using a sonic wave generator (Powersonic410, Hwason Tech).

2. Culture of preadipocyte and differentiation induction of adipocyte

3T3-L1 preadipocyte was cultured at conditions of 37° C. and 5% $CO_2$ in DMEM (Dulbecco's modified Eagle's medium, WELGENE, Korea) in which 10% BCS (Bovine Calf Serum), 100 unit/mL of penicillin, and 100 ng/mL of streptomycin are included. To induce adipocyte differentiation of the 3T3-L1 preadipocyte, when the cells are evenly grown on a 60 mm plate, medium exchange was carried out with DMEM medium in which MDI (10 μg/mL insulin, 1μM dexamethasone and 0.5 mM IBMX (Sigma, USA)) as an agent for inducing differentiation, 10% FBS (Fetal Bovine Serum), 100 unit/mL of penicillin, and 100 ng/mL of streptomycin are included, and the pine needle extract was also treated at that time. After that, with an interval of 2 days, medium exchange was carried out with DMEM medium in which 10 μg/mL of insulin, 10% FBS (Fetal Bovine Serum), 100 unit/mL of penicillin, and 100 ng/mL of streptomycin are included, and the differentiation was induced for 6 days.

TABLE 1

| | Condition for inducing adipocyte differentiation | | | | |
|---|---|---|---|---|---|
| | Cell culture | Induction of adipocyte differentiation | | | |
| Medium composition | DMEM (BCS) | DMEM (FBS) MDI | DMEM (FBS) Insulin | DMEM (FBS) Insulin | DMEM (FBS) Insulin |
| Extract of pine needle juice powder | X | ○ | ○ | ○ | ○ |
| Time | 0 Day | 2 Days | 4 Days | 6 Days | 8 Days |

3. Measurement of preadipocyte's ability of differentiation into adipocyte

Ability of differentiation into adipocyte was measured by using Oil-red O staining method. The 3T3-L1 preadipocyte differentiated into adipocytes was washed 2 to 3 times using PBS (Phosphate-buffered saline) and fixed for 30 minutes by using 10% formaldehyde. Then, it was further fully washed 2 to 3 times using PBS and stained for 1 hour using Oil-red O staining agent which has been dissolved in 60% isopropanol at 5 mg/mL. After the staining, the residual staining agent was fully washed 2 to 3 times using PBS, and the degree of staining was determined using a microscope. After that, the stained Oil-red O was completely dissolved out using 100% by isopropanol, and the ability of differentiation into adipocyte was measured using an UV spectrophotometer (spectrophotometer, BioTec, Eon).

4. Culture and classification of test animals

After recirculating culture period of 7 days, 4-week old male ICR mouse as a test animal was bred under conditions including temperature of 23±3° C., relative humidity of 50±5%, and lighting for 12 hours (i.e., light from 9 AM to 9 PM). After observing general symptoms during the recirculating culture period, healthy animals not showing any symptoms and any body weight loss were classified into 3 groups according to randomized blocking design. The classification was made such that Group A is for general diet+distilled water (6 animals), Group B is for high fat diet+distilled water (6 animals), and Group C is for high fat diet +500 mg/kg pine needle juice powder (7 animals).

5. Diet composition for test animals

Both the general diet and high fat diet were provided so as to be freely taken by the animals. Every 3 to 4 days, the supplied food amount and leftover food amount were measured at the same time point, while the animals were allowed to freely intake distilled water after it is filtered through a microfiltration device. Group A and Group B were provided with 100 μl of distilled water, while Group C was provided with pine needle juice powder (500 mg/kg) after it is dissolved in 100 μl of distilled water in accordance with body weight. As for the oral administration, it was carried out once a day at the same hour (between hour 18 to hour 19). By observing a change in body weight during the test period, an increased amount of the body weight was compared among each groups.

6. Method for supplying diet for each group

The oral administration was carried out by using a sonde (length: 10 cm, thickness: 5 mm), and as primary distilled water using distillator, distilled water which has been sterilized by using a syringe filter was used.

7. Collection and analysis of blood serum sample from test animals

In order to prevent a variation in blood, the animals were subjected to fasting one day before blood sampling (i.e., before 18 hours). For collecting blood, the mouse was anesthetized, and blood was sampled from the eye ball. The sampled blood was immediately kept in ice for storage, and after the collection, the blood was centrifuged for 15 minutes at 4° C., 12,000 rpm by using a low temperature centrifuge. Accordingly, blood serum was separated after the centrifuge. The separated blood serum was kept at −20° C., and then determined in terms of the content of total lipid, total cholesterol, and triglyceride in blood. The blood analysis of the present invention was carried out by Green Cross Corporation.

8. Method for measuring weight of white adipose tissue

In order to find out the effect of various samples that are used for the test on a mouse, weight of the fat was measured and also shape of organs and presence or absence of any lesions were observed. In order to measure the body fat lowering effect, weight of the white adipose tissue present in epididymis was measured.

In order to have the weight measurement, the animals were fasted for 18 hours, and after cervical dislocation, the abdomen of the animal was open. At the same time of separating fats of epididymis, shape of each organ and presence or absence of any lesions were observed. The separated adipose tissue was weighed by using a microbalance, and the white adipose tissue was fixed by using 4% paraformaldehyde.

Example 1. Effect Of Inhibiting Adipocyte Differentiation By Extract Of Pine Needle Juice Powder Depending On Type Of Pine Tree To compare the ability of inhibiting adipocyte differentiation by pine needle juice powder depending on type of pine tree, pine needle juice powder was prepared according to the above production method by using pine needles of a red pine tree and a sea pine tree. Thereafter, a hot water extract was prepared therefrom. The ability of a hot water extract (400 μg/mL, 200 μg/mL and 100 μg/mL) of pine needle juice powder for inhibiting adipocyte differentiation depending on type of pine tree was measured all at the same conditions. As a result, as shown in FIG. 1, the hot water extract of pine needle juice powder of a red pine tree and a sea pine tree exhibited concentration-dependent ability of inhibiting adipocyte differentiation. In particular, under the high concentration treatment, the red pine tree exhibits the ability of inhibiting adipocyte differentiation, i.e., 41% less adipocyte differentiation compared to the control group.

Example 2. Effect Of Inhibiting Lipid Differentiation By Extract Of Pine Needle Juice Powder Of The Present Invention In Example 2, a comparative test was carried out regarding the ability of inhibiting lipid differentiation by preparing each of an extract of dry pine needle of a red pine tree having no juicing process and an extract of pine needle juice powder obtained after juicing process, and also regarding the ability of inhibiting lipid differentiation by an extraction solvent (distilled water and 95% (v/v) ethanol). The descriptions relating to juicing and preparation of powder as employed in the present example are as described above, and as for the dry pine needle, pine needles were completely dried in a cool dark place until the entire moisture evaporated, and then used. As shown in the following Table 2, it was possible to confirm that the yield is significantly higher with the extract of pine needle juice powder (hot water extract and ethanol extract) compared to the extract of dry pine needle (hot water extract and ethanol extract).

TABLE 2

Result of measuring yield with extract of pine needle juice powder of the present invention

| | Pine needle juice powder of red pine | | Dry pine needle of red pine | |
|---|---|---|---|---|
| | Hot water | Ethanol | Hot water | Ethanol |
| Solvent for extraction | 30 g + 270 mL | 30 g + 270 mL | 30 g + 270 mL | 30 g + 270 mL |
| Method for extraction | | 60° C., sonication, 16 h | | |
| Concentration | Freeze drying | Concentration at high temperature and reduced pressure | Freeze drying | Concentration at high temperature and reduced pressure |
| Yield (mg/mL) | 78 mg/ml | 60.4 mg/ml | 15.2 mg/ml | 18.6 mg/ml |

Figure 2:
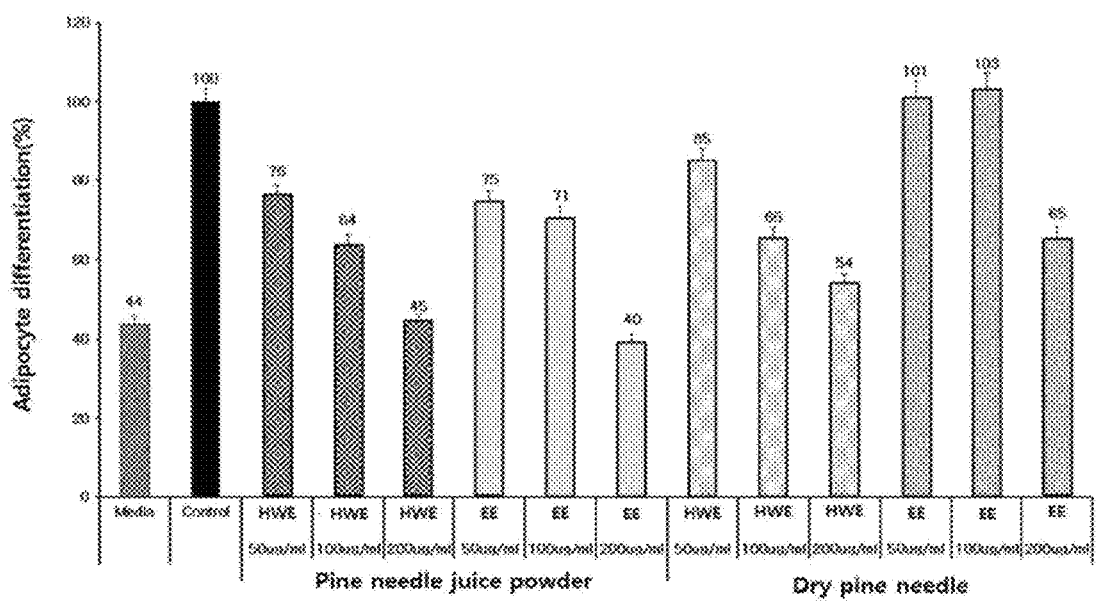
FIG. 2 is a drawing illustrating the inhibitory activity on differentiation of an adipocyte when 3T3-L1 preadipocyte is treated with an extract of pine needle juice powder (i.e., hot water extract(HWE) and ethanol extract(EE)) and an extract of dry pine needle of red pine tree (i.e., hot water extract and ethanol extract), respectively.

As a result of comparing the ability of inhibiting lipid differentiation between an extract of pine needle juice powder of a red pine tree (hot water extract and ethanol extract) which has been obtained by pine needle juicing treatment and an extract of dry pine needle (hot water extract and ethanol extract) of a red pine tree, it was found that, although both the extract of pine needle juice powder (hot water extract and ethanol extract) and extract of dry pine needle (hot water extract and ethanol extract) have an ability of inhibiting lipid differentiation, the extract of pine needle juice powder of the present invention has a significantly higher ability of inhibiting lipid differentiation compared to the extract of dry pine needle (FIG. 2).

Figure 3:
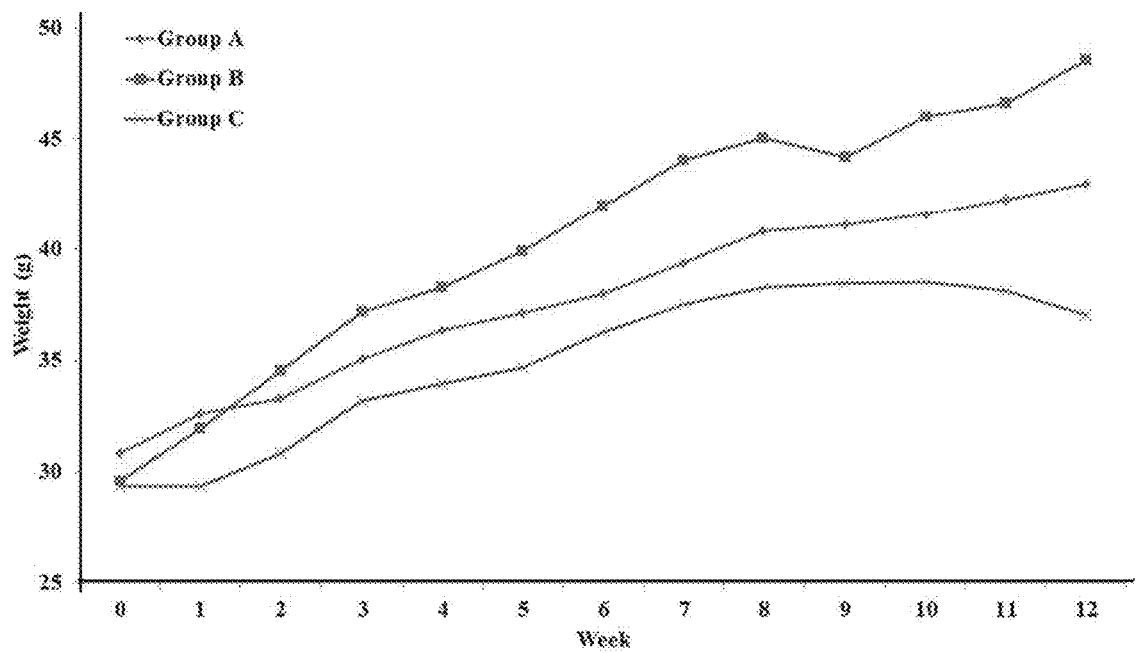
FIG. 3 shows the result of determining a change in body weight according to oral administration of the pine needle juice powder of the present invention, in which the results are shown for each time period (i.e., 0 to 12 weeks). Group A and Group B are a control group for determining the effect in a group administered with the pine needle juice powder of the present invention in which Group A is a general diet group and Group B is a high fat diet group. Meanwhile, Group C is a group under high fat diet with administration of 500 mg/kg pine needle juice powder.
Figure 4:
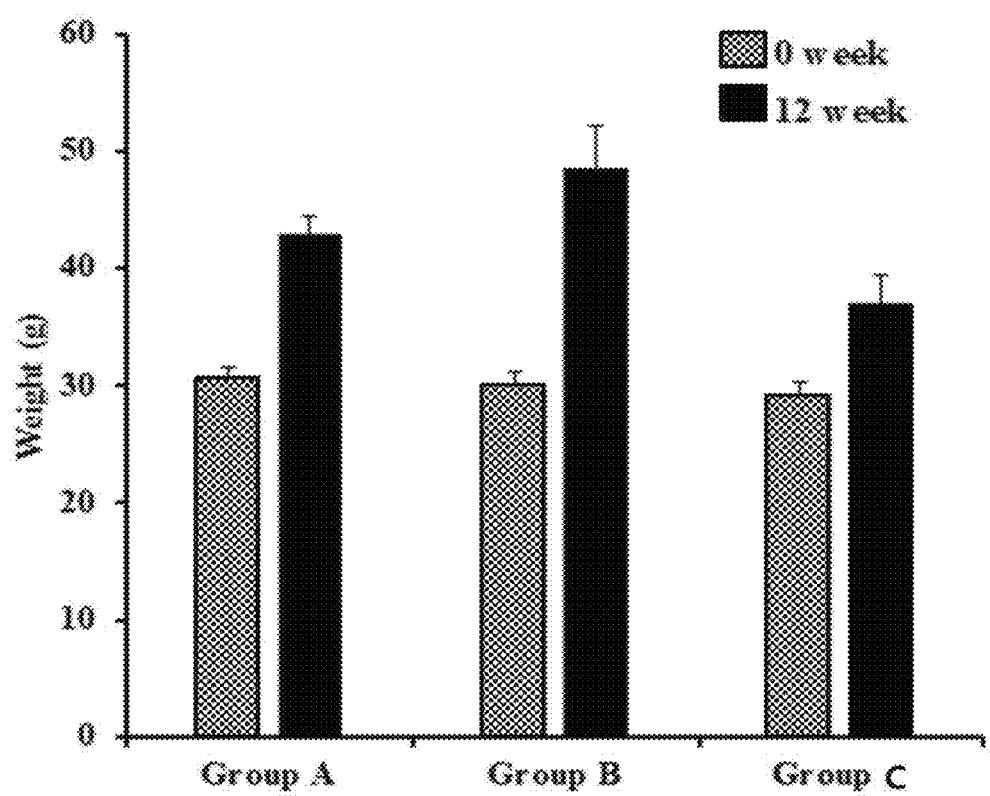
FIG. 4 shows the result of determining a change in body weight before (i.e., 0 week) and after the oral administration (i.e., 12 week) of the pine needle juice powder of the present invention. Group A and Group B are a control group for determining the effect in a group administered with the pine needle juice powder of the present invention in which Group A is a general diet group and Group B is a high fat diet group. Meanwhile, Group C is a group under high fat diet with administration of 500 mg/kg pine needle juice powder.

Example 3. Measurement Of Change In Body Weight According To Administration Of Pine Needle Juice Powder An ICR mouse was orally administered with pine needle juice powder (500 mg/kg) for 12 weeks. The final weight after 12 weeks was as follows: Group A (general diet+distilled water); 42.99±1.41 g, Group B (high fat diet+distilled water); 48.55±3.54 g, and Group C (high fat diet+pine needle juice powder); 37.05±2.39 g. As a result of the aforementioned diet for 12 weeks, it was confirmed that obesity is naturally induced in Group B with high fat diet, while the diet group with pine needle juice powder (500 mg/kg) for 12 weeks was found to have, after the 12 week diet, the body weight that is 11.5 g less than Group B. In particular, it was found that Group B (high fat diet+distilled water) which has been induced to have obesity shows a constant increase in body weight after starting the diet, while Group C (high fat diet+pine needle juice powder) shows, after starting the diet, a reduced body weight increase compared Group B (FIG. 3). The body weight change for each group after 12 weeks was as follows: Group A (general diet+distilled water); 12.14±0.98 g, Group B (high fat diet+distilled water); 18.94±3.86 g, and Group C (high fat diet+pine needle juice powder); 7.66±2.30 g (FIG. 4).

Example 4. Analysis Of Change In Weight Of White Adipose Tissue According To Administration Of Pine Needle Juice Powder After the diet for 12 weeks, the presence or absence of lesions in an internal organ was determined by a naked eye after the dissection. The white adipose tissue was collected and weight of the tissue was measured.

Figure 5:
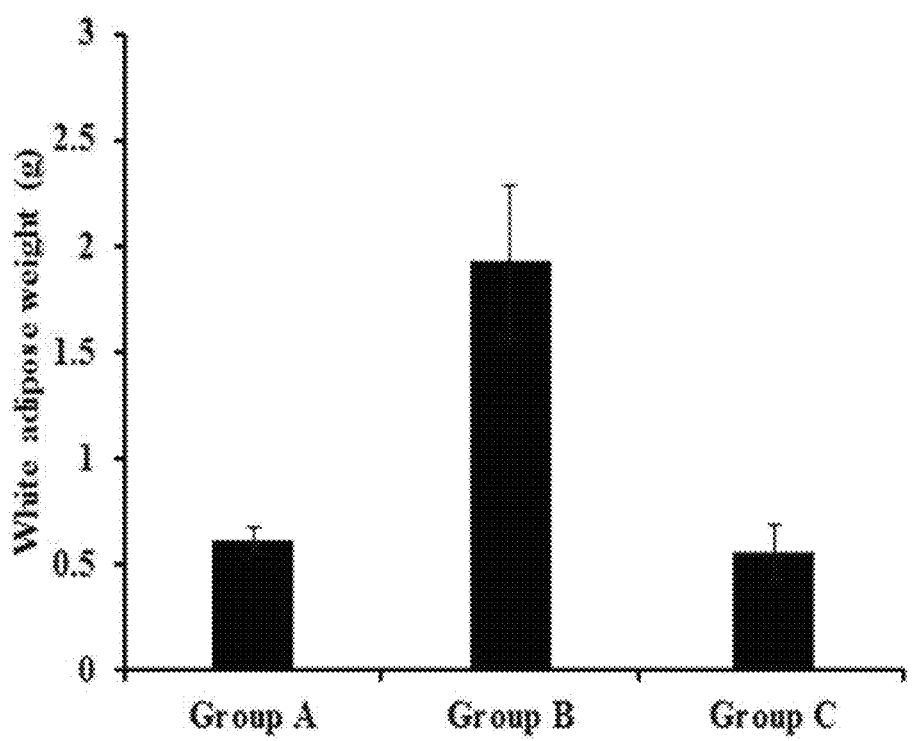
FIG. 5 shows the result of measuring the weight of white adipose tissue after oral administration of the pine needle juice powder of the present invention for 12 weeks. Group A and Group B are a control group for determining the effect in a group administered with the pine needle juice powder of the present invention in which Group A is a general diet group and Group B is a high fat diet group. Meanwhile, Group C is a group under high fat diet with administration of 500 mg/kg pine needle juice powder.

The measured weight of the white adipose tissue is shown in FIG. 5, and it is as follows: Group A (general diet+distilled water); 0.62±0.05 g, Group B (high fat diet+distilled water); 1.93±0.36 g, and Group C (high fat diet+pine needle juice powder); 0.56±0.13 g. Based on these results, it was found that the group administered with the pine needle juice powder for 12 weeks has in-body white adipose tissue which weighs less than the obese Group B.

Example 5. Blood Analysis After Administration Of Pine Needle Juice Powder (Analysis Of Change In Total Lipid, Total Cholesterol, And Glyceride)

After the diet for 12 weeks for each animal group, the effect of the pine needle juice powder was evaluated based on blood analysis. Blood from each group was analyzed by Green Cross Corporation.

Figure 6:
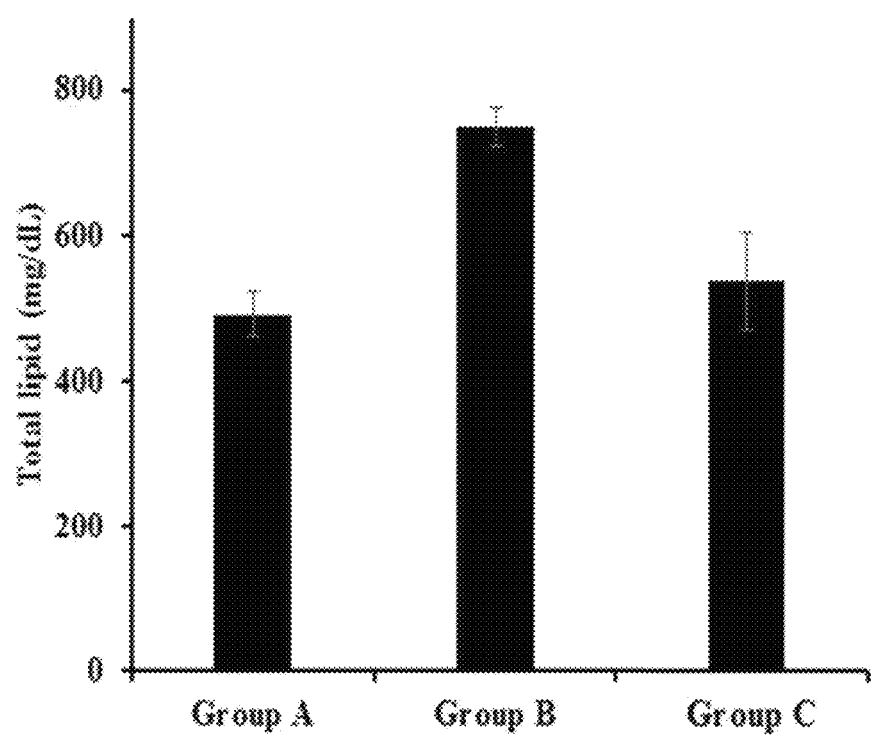
FIG. 6 shows the result of measuring the content of total lipid in blood after oral administration of the pine needle juice powder of the present invention for 12 weeks. Group A and Group B are a control group for determining the effect in a group administered with the pine needle juice powder of the present invention in which Group A is a general diet group and Group B is a high fat diet group. Meanwhile, Group C is a group under high fat diet with administration of 500 mg/kg pine needle juice powder.
Figure 7:
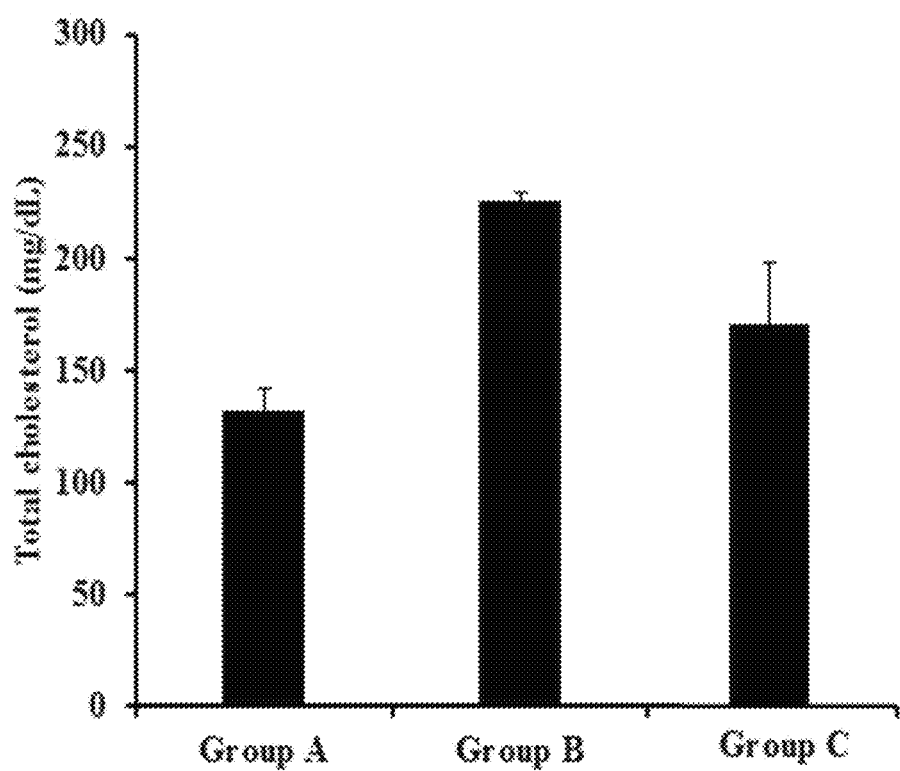
FIG. 7 shows the result of measuring the content of total cholesterol in blood after oral administration of the pine needle juice powder of the present invention for 12 weeks. Group A and Group B are a control group for determining the effect in a group administered with the pine needle juice powder of the present invention in which Group A is a general diet group and Group B is a high fat diet group. Meanwhile, Group C is a group under high fat diet with administration of 500 mg/kg pine needle juice powder.
Figure 8:
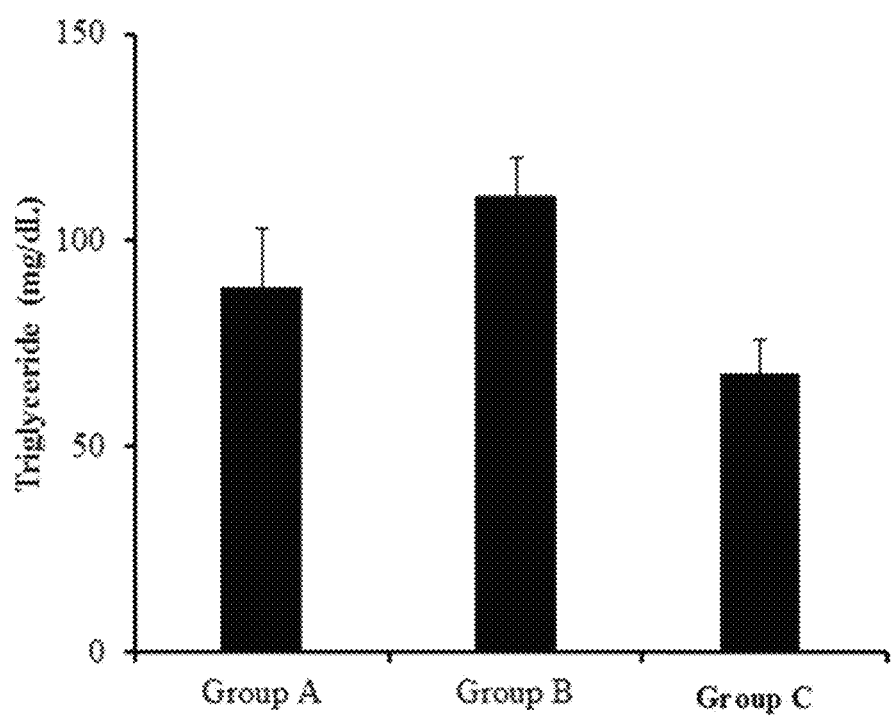
FIG. 8 shows the result of measuring the content of triglyceride in blood after oral administration of the pine needle juice powder of the present invention for 12 weeks. Group A and Group B are a control group for determining the effect in a group administered with the pine needle juice powder of the present invention in which Group A is a general diet group and Group B is a high fat diet group. Meanwhile, Group C is a group under high fat diet with administration of 500 mg/kg pine needle juice powder.

The result of the total lipid analysis is as follows: Group A (general diet+distilled water); 491.25±31.51 mg/dL, Group B (high fat diet+distilled water); 748.67±26.79 mg/dL, and Group C (high fat diet+pine needle juice powder); 536.75±66.44 mg/dL (FIG. 6). The result of the total cholesterol analysis is as follows: Group A (general diet+ distilled water); 132.67±9.29 mg/dL, Group B (high fat diet+distilled water); 225.67±4.19 mg/dL, and Group C (high fat diet+pine needle juice powder); 170.25±27.77 mg/dL (FIG. 7). The result of the triglyceride analysis is as follows: Group A (general diet+distilled water); 88.25±14.67 mg/dL, Group B (high fat diet+distilled water); 111.00±8.92 mg/dL, and Group C (high fat diet+pine needle juice powder); 67.60±8.27 mg/dL (FIG. 8).

Based on the results described above, it was found that Group C administered with the pine needle juice powder for 12 weeks showed significantly decreased content of total lipid, total cholesterol, and triglyceride compared to Group B as a group with obesity.

The invention claimed is:

1. A method of preventing or treating obesity, the method comprising administering a composition comprising a pine needle juice powder to a subject having the obesity,
   wherein the pine needle juice powder is produced by the following steps:
1) preparing pine needle juice by juicing pine needles;
2) freeze-drying the pine needle juice; and
3) pulverizing a freeze-dry product of the pine needle juice obtained by freeze-drying to give pine needle powder.

2. The method of claim 1, wherein a step of extracting pine needle juice powder is further included after the above step 3),
   wherein the step 1) comprises steps of:
a) completely removing moisture on surfaces of the pine needles by using a dehydrator; and
b) extracting juice from the dried pine needles;
   wherein the step 2) comprises steps of:
c) pre-freeze drying at around −50°C.; and
d) removing moisture from the pine needle juice by operating a vacuum pump at −70 to −85° C.

3. The method of claim 2, wherein the extraction of pine needle juice powder is carried out by ultrasonication for 12 to 20 hours at a temperature of 50 to 70°C. by using water, lower alcohol with 1 to 4 carbon atoms, or a mixture solvent thereof.

4. The method of claim 1, wherein the pine needle is a pine needle of red pine (Pinus densiflora).

5. The method of claim 1, wherein the pine needle juice powder inhibits differentiation of an adipocyte.

6. The method of claim 1, wherein the composition is a health functional composition.

7. The method of claim 6, wherein the composition comprises at least one selected from a nutritional agent, vitamin, an electrolyte, a flavoring agent, a coloring agent, an enhancing agent, pectinic acid and a salt thereof, alginic acid and a salt thereof, an organic acid, a protective colloidal thickening agent, a pH adjusting agent, a stabilizer, a preservative, glycerin, alcohol, and a carbonating agent used for carbonate drink in addition to the pine needle juice powder.

8. The method of claim 1, wherein the composition is a pharmaceutical composition.

9. The method of claim 8, wherein the composition further comprises a carrier, an excipient, or a diluent in addition to the pine needle juice powder.

* * * * *